United States Patent [19]

Huizer

[11] Patent Number: 4,722,865
[45] Date of Patent: Feb. 2, 1988

[54] POLY(METH)ACRYLIC NETWORK COATED BIOLOGICALLY OR CHEMICALLY ACTIVE SUBSTRATE AND METHOD OF MAKING SAME

[75] Inventor: Leendert Huizer, Zoetermeer, Netherlands

[73] Assignee: Nederlandse Centrale Organisatie Voor Toegepast-Natuurwetenschappelij-konderzoek, The Hague, Netherlands

[21] Appl. No.: 726,505

[22] Filed: Apr. 24, 1985

[30] Foreign Application Priority Data

Apr. 27, 1984 [NL] Netherlands ............... 8401362

[51] Int. Cl.$^4$ .................................... B05D 3/06
[52] U.S. Cl. ..................... 428/407; 424/419; 424/417; 427/2; 427/3; 427/54.1; 427/213; 427/221; 428/402
[58] Field of Search .............. 427/44, 54.1, 212, 213, 427/213.34, 221, 2, 3; 424/19, 22, 20; 428/402, 403, 407

[56] References Cited

U.S. PATENT DOCUMENTS

| | | | |
|---|---|---|---|
| 3,386,851 | 6/1968 | Harlan | 427/221 |
| 3,661,620 | 5/1972 | Dekking et al. | 427/221 |
| 3,694,253 | 9/1972 | Gerber et al. | 427/53.1 |
| 3,857,932 | 12/1974 | Shepherd et al. | |
| 3,904,745 | 9/1975 | Cohen et al. | 424/21 |
| 3,967,006 | 6/1976 | Yamasuchi et al. | 427/221 |
| 4,007,258 | 2/1977 | Cohen et al. | 424/22 |
| 4,178,361 | 12/1979 | Cohen et al. | 424/22 |
| 4,180,598 | 12/1979 | Emmons | 427/54.1 |
| 4,209,371 | 6/1980 | Lee | 427/54.1 |
| 4,321,117 | 3/1982 | Kaetsu et al. | 424/22 |
| 4,359,483 | 11/1982 | Kaetsu et al. | 427/2 |
| 4,379,038 | 4/1983 | Kaetsu et al. | 424/22 |
| 4,411,754 | 10/1983 | Kaetsu et al. | 424/22 |
| 4,490,436 | 12/1984 | Kawakami et al. | 424/22 |
| 4,572,833 | 2/1986 | Pedersen et al. | 427/3 |
| 4,574,080 | 3/1986 | Roswall et al. | 427/3 |

FOREIGN PATENT DOCUMENTS

| | | |
|---|---|---|
| 1254162 | 10/1960 | Fed. Rep. of Germany . |
| 1257801 | 8/1962 | Fed. Rep. of Germany . |
| 1248687 | 8/1962 | Fed. Rep. of Germany . |
| 1250456 | 8/1962 | Fed. Rep. of Germany . |
| 1270579 | 11/1962 | Fed. Rep. of Germany . |
| 1242573 | 12/1964 | Fed. Rep. of Germany . |
| 1592655 | 7/1966 | Fed. Rep. of Germany . |
| 7440048 | 12/1973 | France . |
| 750809 | 7/1952 | United Kingdom . |
| 1269018 | 3/1972 | United Kingdom . |
| 2017113 | 10/1979 | United Kingdom . |
| 543250 | 3/1980 | U.S.S.R. . |

OTHER PUBLICATIONS

Ohi, Kazuhiko; Slow-Release Fertilizer, Chemical Abstracts, vol. 78, 1973, p. 410.
Kirk-Othmer, Enc. of Chem. Techn., 3rd edition, vol. 17, 1982, pp. 304, 309.
Product Information for Vydate, Dupont.
Product Information for Photomer, 3049 and 4127, Diamond Shamrock.
Product Information for Vorlhuflges Merkblatt, Degussa.
Minoru Kumakura and Isao Kaetsu, Influence of Hydration Ability of Monomer of Microbial Cells by Radiation Polymerization; Journal of Applied Polymer Science, vol. 28, pp. 2167-2175, (1983).
Ullmann Enc. der Sechn Chemie, vol. 10, 4th Ed., 1975.
Product Information for Irgacure, 651.
Product Information for Radcure Products.

*Primary Examiner*—John H. Newsome
*Attorney, Agent, or Firm*—Brumbaugh, Graves, Donohue & Raymond

[57] ABSTRACT

A solid substrate, which contains or consists of a biologically or chemically active substance, is coated with coating material containing at least one polymerizable crosslinkable polyfunctional acrylic or methacrylic compound whereafter the coating material is subjected to polymerization substantially in the absence of non-polymerizable components to form a network coating of polymer on the surface of the solid substrate. This coating permits either the controlled release of active substance from the coated substrate or the controlled access of material reacting with said active substance into the coated substrate and the controlled release of the resulting reaction products from the coated substrate.

22 Claims, No Drawings

POLY(METH)ACRYLIC NETWORK COATED BIOLOGICALLY OR CHEMICALLY ACTIVE SUBSTRATE AND METHOD OF MAKING SAME

The invention relates to a substrate which consists at least partially of a biologically or chemically active substance and at least part of the surface of which is coated with a permeable network coating of a polymer. This coating permits either the controlled release of active substance from the coated substrate or the controlled access of material reacting with said active substance into the coated substrate and the controlled release of the resulting reaction products from the coated substrate. The invention also relates to a process for providing said coated substrate.

It is known to provide substrates containing an active substance with a coating permitting the active substance to be released to the environment in a controlled manner.

Coating particulate fertilisers in this way is generally known. Reference may be made to a review article in Ullmanns Enzyklopaedie der technischen Chemie, 4th edition, volume 10 (1975), page 233 and to the literature cited therein. According to British Pat. No. 750,807, a fertiliser is, for example, mixed with a solution of a polymer of a polar vinyl compound in an organic solvent. After removal of the solvent, the particles are found to be coated with a layer of the polymer.

It is known from German Pat. No. 1,248,687 that fertilisers can be coated using aqueous solutions which contain a mixture of a precondensate of from 20 to 80% by weight of an aminoplast precondensate and 80 to 20% by weight of a copolymer of from 50 to 90% by weight of an ester of acrylic acid or methacrylic acid with a monovalent, non-polymerizable alcohol, 5 to 30% by weight of an $\alpha,\beta$-ethylenically unsaturated mono- or dicarboxylic acid and 2 to 45% by weight of other monomeric copolymerizable compounds, whereas according to German Pat. No. 1,250,456 an aqueous solution of a mixture of from 20 to 80% by weight of an aminoplast precondensate and 80 to 20% by weight of a polyester component is used. After the coating of the fertilisers with the aqueous solutions, the components of these solutions harden to form a coating layer on the fertiliser particles.

For coating fertiliser particles, according to German patent application Nos. 1,242,573 and 1,254,162, copolymers of dicyclopentadiene and drying or semi-drying oils are used, and according to German patent application No. 1,270,579, drying oily polyene polymers, which are isomerised under the influence of catalysts and are dried after application onto the particles, are used.

According to German Pat. No. 1,467,383, a mixture of a polyene polymer containing free vinyl groups with a drying oil and a lipophilic aminoplast condensate is used. According to German Pat. No. 1,592,655 organic substances, which swell in water, or finely divided salts, oxides and/or metals are incorporated in plastic coatings which are intended for coating fertiliser particles. According to French Pat. No. 2,253,553, a plastic which is degradable under the influence of ultraviolet light is used for coating fertilisers.

From Chemical Abstracts, vol. 78 (1973), page 410, abstract 28544q it is known to mix fertiliser granules with an aqueous acrylamide solution and to expose the mixture to $\gamma$-radiation thus giving a polymerized slow release fertiliser with low hygroscopicity. However, by this process a water soluble coating of a linear polymer is formed upon the fertiliser granules, which does delay the release of the fertiliser into the soil after the fertiliser granules have been brought therein, but does not permit the controlled release of the fertiliser for an extended period of time. Once the polyacrylamide has been dissolved from the granules the whole fertiliser content of the granules becomes active immediately.

It is likewise known to coat drugs with polymers in order to ensure that the release of the drug in the gastrointestinal tract can be controlled accurately. Reference may be made to Kirk-Othmer's Encyclopedia of Chemical Technology, 3rd edition, volume 17 (1982), page 304 and to the literature references cited therein.

In the processes for coating particles to permit the controlled release of an active substance as described hereinabove, aqueous or organic solutions of polymers as well as oily mixtures have been used. The disadvantage of these known processes is that the solvent must be removed or drying and hardening must be effected for a fairly long time. In the course thereof, a state always occurs in which the coating of the particles is viscous and/or tacky, as a result of which the particles adhere to each other, which leads to the formation of agglomerates as well as to the damage of the coating layer applied. The disadvantage of damaging the coating layers can, it is true, be overcome by applying more than one such layer, but the disadvantage of the possibility of agglomerate formation still persists.

The disadvantage as described hereinbefore is also encountered when using the process of the French Pat. No. 1,081,591 for coating granules of hygroscopic substances. In this process small amounts of a polymeric vinyl compound are added to these granules, which vinyl compound is generally dissolved in water or an organic diluant or suspended or emulsified in water. The resulting coating prevents the agglomeration of the hygroscopic granules. According to the French Pat. No. 1,081,591 it is also possible to add the vinyl compound as a monomer to the granules and then polymerize it in situ. However, the disadvantage of this embodiment is that the vinyl compounds used are liquids with a very low viscosity, so that a considerable amount of vinyl compound must be used to obtain a sufficient coating, which coating moreover will appear to be very irregular. If one would use this process for coating granules containing an active substance, which should be released to the environment, the release will be unsatisfactory in view of the thick layer, which moreover does not form a proper network.

It is further known from the USSR Pat. No. 543,250 to treat fertiliser granules with a monomer or a monomer mixture in the gas state. An example has been given of coating urea granules by contacting them with a methylmethacrylate vapour whilst subjected to $\delta$-radiation at 60° C. In this way a coating of a linear polymer is formed upon the granules, which does delay the release of the fertiliser, but is not satisfactory to control the release of the fertiliser from the granules. If the process described in this USSR Patent would be used with liquid methylmethacrylate the same disadvantages would be encountered as described with the process of the French Pat. No. 1,081,591, namely that in view of the very low viscosity of the methylmethacrylate a very thick and/or irregular coating would be formed upon the granules, which is not suitable either for permitting controlled release of the fertiliser to the environment.

It is known from the British Pat. No. 1,269,018 to coat pulverulent materials with a polymer by subjecting the pulverulent material to a high frequency electrical discharge under reduced pressure in the presence of at least one polymerizable organic compound which is in the liquid or gaseous state or may be dissolved in a solution. As examples of polymerizable compounds monomers having a very low viscosity are mentioned. A great amount of said monomer is necessary to form a complete coating and said complete coating is too thick to permit the desired controlled release of active substance present within the coating of the polymer.

It has now been found that a solid substrate, which consists at least partially of a biologically or chemically active substance and at least part of the surface of which is coated with a permeable network coating on the base of a water insoluble acrylic or methacrylic polymer, has very desirable properties with respect to the possibility of the controlled release of the active substance present or with respect to the controlled access of material reacting with said active substance into the coated substrate and the controlled release of the resulting reaction products from the coated substrate. The process which provides such a coated substrate does not make use of polymer solutions or emulsions. The process comprises contacting the surface to be coated of the solid substrate with a coating material containing at least one polymerizable crosslinkable polyfunctional acrylic or methacrylic compound and subjecting the coating material to polymerization substantially in the absence of non-polymerizable components.

Since the process according to the invention is carried out in the substantial absence of non-polymerizable components, there is no need of removing volatile compounds, such as solvents.

The substrates to be coated may be of any shape and dimension. In practice in general fibers, films and especially granules containing active substances will be coated. It is not always necessary or desirable to coat the complete surface of the substrate containing the active substance. This substrate can e.g. be anchored upon solid supports and in that case only the surfaces exposed to the environment should be coated. The way of coating, the thickness and the strength of the resulting coat are in most cases determined by the nature of the active substance in the substrate.

The biologically or chemically active substance which is present in or forms the substrate can in fact be of any nature. Examples of these substances are drugs of any kind, flavouring agents, fragrances, agrochemicals, such as herbicides, insecticides, fungicides, nematicides, fertilisers, soil improving agents, plant growth regulators etc. In many cases the coating is applied not to pure active substances, but to preparations or formulations of these active substances. The formulations or preparations may contain any of the known diluents, surface active agents and other additives known in the art. The active substances as described hereinabove can be released from the coated compositions in a controlled way.

It is further feasible to coat solid catalyst compositions with an acrylic or methacrylic polymer so as to make it possible that the catalyst deploys its activity in a controlled way, being released to the system to be catalyzed only gradually. The same holds for solid enzyme containing compositions, which might be coated in such a way that the enzyme is hold back within the coating, but a medium, preferably a liquid medium, such as an aqueous medium, which contains the substance to be subjected to the action of the enzyme, is admitted from the outside into the coated composition, which then releases in a controlled way to the environment of the product obtained by the enzymatic action in the medium. Similar considerations apply to solid compositions containing micro-organisms, bacteria etc. It therefore appears that the substrate may also contain the active substance immobilized. In these cases it is the medium of the environment, which will be in most cases liquid, but which may also be gaseous, that penetrates through the network coating, acts upon or reacts with the active substance and transports resulting products outside of the coating solid substrate. The broad spectrum of possibilities of coating solid substrates is based on the substantially unlimited variability of the type and structure of the network formed on the substrate as described in the above, which means that for any specific purpose a suitable coating can be developed by varying the types and/or proportional amounts of the ingredients of the coating material.

The acrylic and methacrylic compounds used in the process of the invention are called polyfunctional, because the suitable coating materials must have two or more (meth)acrylic groups, since otherwise they do not form a network upon polymerisation. Thus, compounds such as acrylamide or methylmethacrylate are not suitable. Suitable compounds may e.g. by represented by the general formulae $R-(-CO-C=CH_2)_n$ or $R-(-CO-C(CH_3)=CH_2)_n$. In these formulae n represents an integer of at least 2 and is preferably 2, 3 or 4. R is e.g. the moiety of a polyalcohol or polyamine, with which the (meth)acryl moieties form the coating material. This polyalcohol or polyamine may be a monomeric compound, e.g. 1.6-n-hexanediol, trimethylolpropane or pentaerytritol or similar amine compounds, an oligomeric compound, such as a dimeric, trimeric or tetrameric compound, or a more complex reaction product as may appear from the specific examples given hereinafter. These coating materials are in some cases prepolymers having specific (meth)acrylic functionalities. All (meth)acrylic polymers will be further referred to as (meth)acrylates, also when they could be considered as amides.

A number of the coating materials useful in the process of the invention is known. However, these known compounds have not been used for the present purpose. Examples of known coating materials, which are suitable for the process of the invention are urethane-acrylates, such as those marketed under the trademarks Ebecryl (UCB, Drogenbos, Belgium) and Photomer (Diamond Shamrock Corp.), epoxy-acrylates, such as those marketed under the trademarks Ebecryl, Photomer and Laromer (BASF, Ludwigshafen, Federal Republic of Germany) and VPS (Degussa, Frankfurt, Federal Republic of Germany), polyester-acrylates, such as those marketed under the trademark Laromer, polyether-acrylates, as well as amine-acrylates, such as those marketed under the trademark Uvecryl (UCB, Drogenbos, Belgium). These (meth)acrylates are liquid products.

The viscosity of the coating materials which hereinafter are also referred to as lacquers, is very important. If the viscosity is too low, the lacquer used is too thin and the coat applied is quickly damaged. If the viscosity is too high, the particles can easily adhere to each other. The most suitable viscosity is also determined by the coating technique employed and by the type of the substrate coated. Therefore, absolute quantitative data for the viscosity are difficult to give. In practice an expert can determine the most suitable viscosity by means of simple tests. The viscosity can also be adjusted by using mixtures of coating materials, in which case it is also true for each mixture that it influences the rate of release of the active substance from the substrate or the access of reacting medium into the substrate.

The thickness of the final lacquer coat is dependent on the type of the coating material and/or of the substrate used and on the rate of release desired and may be varied within wide limits, for example, between 5 and 100 μm. Said thickness can be easily determined by the expert in the art.

Examples of low viscosity coating materials are triisopropyleneglycoldiacrylate, 1,6-n-hexadioldiacrylate and trismethylolpropanetriacrylate. These acrylates are copolymerized with the more viscous acrylates, which can be solved therein.

In a number of cases it may be advantageous to incorporate in the coating material one or more monofunctional polymerizable monomers so as to modify the properties of the coating material or of the resulting coat. These monofunctional compounds, which may also be (meth)acrylates, as such do not form a network, when subjected to polymerization, but modify the network formed by the polyfunctional (meth)acrylates with which they are copolymerized. Examples of such monofunctional monomers are acrylic acid, methacrylic acid, (meth)acrylic esters, N-vinylpyrolidone, vinypyridine and styrene. These compounds copolymerize with the crosslinkable acrylates or methacrylates or are at least immobilized in the coating layer obtained upon the substrate.

During coating, a network is formed upon the surface coated. Determining factors for the effectiveness of the network in the controlled release of active substance from the substrate are, inter alia, the polarity of the crosslinked coating layer, the rigidity or mobility of the polymer chains in the network, the mesh width in the network and the manner in which the material of the network reacts upon the environment into which the coated substrates are introduced. Thus, for example, when using a coating layer which has a slightly polar character, release of an active polar substance from the substrate as a rule occurs slowly. When the coating layer possesses a strongly polar character, more rapid release occurs.

The way of effecting the polymerization is known in the art. The acrylates or methacrylates used as coating materials are polymerized by a free radical mechanism. The polymerization may be a thermal polymerization using a peroxide as an initiator. Preferably, however, the polymerization is carried out under the influence of radiation, which initiates the formation of free radicals. The formation of radicals takes place, for example, directly through the use of electron beams (β-radiation) or of δ-radiation, but can also take place through the use of ultra-violet light. In the last-mentioned case preferably a photoinitiator is added to the coating material. The radiation techniques are known in the art. As photoinitiators to be used together with ultra-violet light, for example, known compounds, such as benzil ketals, benzoin ethers, acetophenone derivatives, ketoxime ethers, benzophenone, benzil or thioxanthones can be mentioned. These photoinitiators may be used, if necessary, together with co-initiators, such as aliphatic tertiary amines. In case of polymerization under the influence of radiation, the polymerization takes place rapidly at ambient temperature, so that heating is not necessary.

In the course of this process for coating substrates with polymers, which are formed in situ on the particles, a state also occurs where the coating is viscous and tacky. However, the period during which the critical viscosity range occurs is so small that the formation of agglomerates, and damage, hardly occurs. This period is in general less than 1 minute and amounts in many cases to 0.2 to 10 seconds, for example 0.5 to 1 second. Due to this extraordinarily rapid hardening of the coating layer, the coating process can be easily carried out continuously. If the coating layer is too thin or has inadequate mechanical strength, the coating process can be repeated once or several times, and in that case different coating materials can also be used for the different coating layers. In this way not only does the coating layer acquire the desired mechanical strength, but it is also possible to control the rate of release of the active substance from the substrate and to adjust it exactly for each separate active substance. By means of experiments, an expert can determine, with respect to each material to be coated and each coating material, the optimal control of the rate of release of the active substance from the substrate.

The coating of the substrate can be carried out continuously or discontinuously. For example, if a particulate material is to be coated, it can be mixed with the lacquer, while stirring cautiously, and subsequently the wet granules can be brought into a fluidized state above a glass filter through which nitrogen is passed. It is also possible to bring the particles to be coated into a fluidized state with the aid of a carrier gas and to introduce thereafter the lacquer used for the coating into the fluidized bed co-currently with the carrier gas, while the whole is subsequently exposed to radiation. The particles coated with the hardened lacquer are then removed from the fluidized bed. It may be noted in this context that the coating of fertiliser granules in a fluidized bed is known per se from German patent application No. 1,257,801 and German patent application No. 1,938,933.

In a number of cases it can be important that the release of the active substance from the coated substrate should not take place immediately. It has been found that in a number of cases the coated substrate shows a certain induction period, that is to say a period in which it is already present in the particular environment in which release of the active substance must occur, but during which no release as yet occurs. This can probably be ascribed to the fact that the coating layer must first be saturated with water from the environment in order that dissolution of the active substance from the substrate can begin. Induction periods of between 1 and 9 hours can readily be achieved.

The following examples serve to illustrate the invention without limiting it to the embodiments shown.

EXAMPLE I

A large number of tests was carried out with regard to the coating of fertiliser granules with lacquers. The results of these tests are reported in Table A. The tests made use of the following starting materials:

Fertiliser

The fertiliser consisted of NPK 19-6-12.

Comparison materials

Osmocote, a product marketed by Sierra Chemical Europe B.V., fertiliser granules provided with a coating layer based on drying oils, dicyclopentadiene and maleic anhydride.

Ebecryl 170 PA, an acrylate derivative having a Höppler viscosity of 5,200 mPa.s at 25° C.

Thinners

NVP, N-vinyl-2-pyrrolidone, a customary commercial product,

TPGDA, triisopropylene glycol diacrylate, a liquid having a hydroxyl number of less than 70, an acid number of less than 1 and a Höppler viscosity of 10–20 mPa.s at 25° C.

HDDA, 1,6-n-hexadiol diacrylate, having a hydroxyl number of less than 25, an acid number of less than 1 and a Höppler viscosity of less than 10 mPa.s at 25° C.

Epoxy-acrylates

Ebecryl 605, a solution of 75% by weight of Ebecryl 600 in TPGDA. Ebecryl 600 is an oligomer of a straight-chain epoxy-acrylate, having a molecular weight of 500 and a Höppler viscosity of 4,000 mPa.s at 60° C.

Ebecryl 605 has a Höppler viscosity of 7,500 mPa.s at 25° C.

Ebecryl 1608, a solution of 80% by weight of Ebecryl 600 in OTA 480, having a Höppler viscosity of 1,000 mPa.s at 60° C.

VPS 1960, a prepolymer resin based on epoxidized soy bean oil, having an acid number of less than 20, a molecular weight of 1.200 and a viscosity of 25,000 mPa.s at 25° C.

Photomer 3049, an aromatic epoxy-acrylic resin modified with fatty acid, having an acid number of 2 and a viscosity of 4,000 mPa.s at 60° C.

Urethane-acrylates

Ebecryl 204, a solution of 75% by weight of an aromatic urethane-acrylate in HDDA, having a Höppler viscosity of 17,000 mPa.s at 25° C. and a molecular weight of 2,000.

Ebecryl 210, an aromatic straight-chain urethane-acrylate, having a Höppler viscosity of 3.500 mPa.s at 60° C. and a molecular weight of 1,500.

Ebecryl 284, a solution of 88% by weight of an aliphatic urethane-acrylate in HDDA, having a Höppler viscosity of 7,500 mPa.s at 25° C. and a molecular weight of 1,200.

Photomer 4094, an aliphatic trifunctional urethane-acrylate having a viscosity of 100 mPa.s at 25° C. and an acid value of 0.5.

Photomer 4127, an aliphatic difunctional urethane-acrylate, having a hydroxyl number of 40, an acid number of 0.5 and a viscosity of 14–20 mPa.s at 25° C.

Photomer 4149, an aliphatic trifunctional urethane-acrylate having an acid number of 0.5 and a viscosity of 70–85 mPa.s at 25° C.

Polyester-acrylate

Laromer PE 55 F, a polyester-acrylate having a viscosity of 30,000–50,000 mPa.s and an acid number of less than 5.

Polyether-acrylate

A polyether-acrylate having two terminal acrylate groups, as a result of which it is crosslinkable via radical polymerization, was prepared by acrylating a polyether-diol, which contained one polypropylene oxide block, with a polyethylene oxide block on either side. The molecular weight of the polypropylene oxide block was 1,750 and the molecular weight of the polyethylene oxide blocks was 250 in total, so that the total molecular weight was 2,000. The polyether-diol described is commercially available under the trademark Pluriol PE 6100 (BASF, Ludwigshafen, Federal Republic of Germany).

Flow-out agent

Ebecryl 350, a polysiloxane diacrylate having a Höppler viscosity of about 250 mPa.s at 25° C., and an acid number of less than 1.

Ebecryl is a registered trademark of UCB, Drogenbos, Belgium.

VPS is a registered trademark of Degussa, Frankfurt, Federal Republic of Germany.

Photomer is a registered trademark of Diamond Shamrock Corporation.

Laromer is a registered trademark of BASF, Ludwigshafen, Federal Republic of Germany.

All the lacquer compositions used for the tests contained 4% by weight of the photoinitiator Irgacure 651 (a registered trademark of Ciba-Geigy, Basle), benzildimethylketal.

In all tests, the fertiliser granules were coated as follows with the lacquer. The lacquer was added to the granules, with cautious stirring. Thereafter, the wet granules were brought into a fluidized state on a glass filter through which nitrogen was passed. In this fluidized state, they were irradiated for 3 minutes by means of six tubular low pressure mercury lamps emitting UV radiation between 300 and 460 nm. The fluidized state only occurs after the lacquer has partially hardened. In a number of cases, the coating with the lacquer, in the manner described, is repeated once or several times in order to restrict the effect of damage of the lacquer coating to a minimum. The thickness of the lacquer layer is shown in Table A.

After the fertiliser granules have been coated with the lacquer, the rate of release of the fertiliser from the granules to demineralised water is measured via the conductivity at 20° C. To that end, 150 ml of water are pumped continuously, by means of a peristaltic pump, at a speed of 35 ml per minute, through a bed of 30 g of granules and through the measuring cell of a conductivity meter, by which the conductivity is continuously recorded. The rate of release is the mean rate of dissolution, measured in the period after the induction period, until 50% of the fertiliser originally present in the granules has dissolved. The rate of release is given as the weight of the fertiliser dissolved per minute, expressed as a percentage of the weight of the fertiliser originally present in the granules.

Table A shows that the rate of release of the uncoated fertiliser is high, as was naturally to be expected. The Osmocote granules provided or not provided with an additional lacquer coat, exhibit a very low rate of release.

The epoxy-acrylate lacquers used are themselves so viscous that they can only be employed when using a reactive thinner which is completely immobilized during hardening. Tests E1, E2, E3 and E4 show the influence of the viscosity of the lacquer on the quality of the hardened single lacquer coat. When using a lacquer which is too thin (test E1) or which is too thick (test E4), the rate of release was too high, due to lacquer damage. Using a more suitable viscosity (tests E2 and E3), the lacquer was less damaged, which manifests itself in a much lower rate of release.

Tests E5, E6, E7, E8 and E9 show that after the fertiliser granules have been coated with three layers of lacquer, these granules exhibit a fairly considerable release period, with the rate of release however being greater than that of the Osmocote granules, for which the induction period, on the other hand, is zero.

When using coatings based on urethane-acrylates it is found that the use thereof leads to greatly differing rates of release and induction periods. It appears that in tests U1 to U8 the rate of release is rather high, which is due to the low viscosity of the coating material used. In tests U9, U10, U11, U12, U13 and U14 low rates of release were obtained, which is due to the considerable higher viscosity of the coating material compared with tests U1 to U8. The acrylate content in these cases was however higher than the acrylate content in the epoxy-acrylate lacquers used. In these cases, however, an induction period does not always occur.

Tests U12 and U13 furthermore show that it is also possible to apply lacquer coats of different types in order to control the induction time and the rate of release. Test U14 gives an example of rate of release which is almost the same as that of the comparison material V2.

Test U13 shows that when using a flow-out agent (Ebecryl 350), a top coat having a very long induction period was formed, but on the other hand the rate of release was again somewhat higher.

When using the polyester-acrylate PE 55 F it is found that after 350 minutes the rate of release increases rapidly, namely from about 0.02 to about 0.07.

Table A show clearly that it is possible for an expert to find the optimal coating for each particular case by performing simple tests.

TABLE A

Influence of the lacquer coating composition on fertiliser granules on the induction period and release rate of these granules. All lacquer coats contain 4% by weight of photoinitiator.

I Comparison materials

| Test | | Coat thickness, μm | Induction period, minutes | Release rate |
|---|---|---|---|---|
| V1 | Uncoated fertiliser | 0 | 0 | 20 |
| V2 | Osmocote | 50 | 0 | 0.005 |
| V3 | Osmocote + Ebecryl 170 PA (0.033 g of lacquer/g of fertiliser) | 60 | 0 | 0.00314 |

II Epoxy-acrylates

| Test | Type | Content, % by weight | Thinner | Content, % by weight | Number of coating steps | Loading, g of lacquer/g of fertiliser | Coat thickness, μm | Induction period, minutes | Release rate |
|---|---|---|---|---|---|---|---|---|---|
| E1 | Ebecryl 605 | 25 | NVP | 71 | 1 | | 10 | | 8.0 |
| E2 | Ebecryl 605 | 61 | NVP | 35 | 1 | | 10 | | 0.9 |
| E3 | Ebecryl 605 | 79 | NVP | 17 | 1 | | 10 | | 0.8 |
| E4 | Ebecryl 605 | 87 | NVP | 9 | 1 | | 10 | | 7.0 |
| E5 | VPS 1960 | 24 | TPGDA | 72 | 3 | 0.10 | 50 | 75 | 0.07 |
| E6 | VPS 1960 | 48 | TPGDA | 48 | 3 | 0.10 | 50 | 220 | 0.056 |
| E7 | Ebecryl 1608 | 24 | TPGDA | 72 | 3 | 0.10 | 50 | 150 | 0.063 |
| E8 | Ebecryl 1608 | 48 | TPGDA | 48 | 3 | 0.10 | 50 | 200 | 0.063 |
| E9 | Photomer 3049 | 48 | TPGDA | 48 | 3 | 0.10 | 50 | 160 | 0.049 |

III Urethane acrylates

| Test | Type | Content, % by weight | Thinner | Content, % by weight | Number of coating steps | Loading, g of lacquer/g of fertiliser | Coat thickness, μm | Induction period, minutes | Release rate |
|---|---|---|---|---|---|---|---|---|---|
| U1 | Photomer 4127 | 78.5 | NVP | 17,5 | 2 | | 10 | 2 | 1.33 |
| U2 | Photomer 4127 | 78.5 | NVP | 17,5 | 1 | 0.033 | 10 | 2 | 0.8 |
| U3 | Photomer 4127 | 96 | | | 1 | 0.033 | 10 | 2 | 0.9 |
| U4 | Photomer 4127 | 96 | | | 2 | 0.050 | 15 | 20 | 0.16 |
| U5 | Photomer 4127 | 96 | | | 3 | 0.033 | 10 | 20 | 0.16 |
| U6 | Photomer 4094 | 96 | | | 3 | 0.033 | 10 | 12 | 0.19 |
| U7 | Photomer 4149 | 96 | | | 3 | 0.033 | 10 | 5 | 0.41 |
| U8 | Photomer 4149 | 96 | | | 3 | 0.050 | 15 | 6 | 0.21 |
| U9 | Ebecryl 210 | 64 | TPGDA | 32 | 3 | 0.10 | 50 | 0 | 0.018 |
| U10 | Ebecryl 204 | 64 | TPGDA | 32 | 3 | 0.10 | 50 | 0 | 0.01 |
| U11 | Ebecryl 284 | 64 | TPGDA | 32 | 3 | 0.10 | 50 | 0 | 0.0086 |
| U12 | Ebecryl 284 + VPS 1960 | 78 / 78 | TPGDA / TPGDA | 18 / 18 | 1 + 2 | 0.033 / 0.066 | 50 | 50 | 0.014 |
| U13 | Ebecryl 284 + VPS 1960 | 78 / 78 | TPGDA / TPGDA Ebecryl 350 | 18 / 16 / 2 | 1 + 2 | 0.033 / 0.066 | 50 | 500 | 0.020 |
| U14 | Ebecryl 284 | 78 | HDDA | 18 | 3 | 0.10 | 50 | 0 | 0.006 |

IV Others

| Test | Type | Content, % by weight | Thinner | Content, % by weight | Number of coating steps | Loading, g of lacquer/g of fertiliser | Coat thickness, μm | Induction period, minutes | Release rate |
|---|---|---|---|---|---|---|---|---|---|
| P1 | PE 55 F | 72 | TPGDA | 24 | 3 | 0.10 | 50 | | 0.052 |
| P2 | Polyether-acrylate | 78 | HDDA | 18 | 4 | 0.10 | 50 | 120 | 0.028 |

EXAMPLE II

With the use of the coating method of Example I, but with a HPA 400 lamp (a medium-pressure metal halide lamp emitting UV radiation between 300 and 400 nm) as a radiation source granules of the commercial insecticidal and nematicidal composition Vydate 10 G ® (E. I. du Pont de Nemours & Co.) were coated. This composition is a free-flowing granular product containing as the active compound 10% by weight of oxamyl, which has the chemical name methyl-N',N'-dimethyl-N-[(methyl-carbamoyl)oxy]-1-thio-oxamimidate, which active compound is adsorbed on clay particles.

The test results are listed in Table B. The description of the coating materials can be found in Example I. Each of the coating compositions contained 4% by weight of the photoinitiator Irgacure 651. In each of the tests three coating steps have been used, in each of which the same quantity of lacquer was applied. In each test 15 g of Vydate 10 G particles have been coated and the coated particles have been examined. The release of the oxamyl was determined as follows: The coated particles were brought into demineralized water (10 parts by weight of water per part by weight of coated particles) and the release took place under static conditions. The content of oxamyl in the water phase was determined by high pressure liquid chromatography. The values of the release indicated in Table B are the amounts of oxamyl in the water phase as a weight percentage of the amount originally present in the composition.

From the results given in Table B it appears that already after 1 hour a considerable amount of oxamyl has been released so that by the use of the compositions coated according to the invention immediate protection against insects and nematodes is guaranteed. However, this protection is lasting much longer than the protection provided by the uncoated compositions from which the oxamyl has been released already completely after one hour. When comparing the results of tests 1–4 with the results of tests 5–8 it will appear that the release of oxamyl is retarded when the coat applied is thicker. However, finally all active substance is released in the course of time, which means that the lacquer does not prevent the active substance to leave the granule completely.

TABLE B

| Test | Type | Content % by weight | Thinner | Content % by weight | Number of coating steps | Loading g of lacquer/ g of Vydate 10 G | release (%) after | | | |
|---|---|---|---|---|---|---|---|---|---|---|
| | | | | | | | 1 h | 2 h | 28 h | 48 h |
| 1 | Ebecryl 605 | 79 | NVP | 17 | 3 | 0,3 | 52 | 62 | 80 | 95 |
| 2 | Ebecryl 1608 | 48 | TPGDA | 48 | 3 | 0,3 | 53 | 53 | 57 | 85 |
| 3 | Photomer 4127 | 96 | | | 3 | 0,3 | 50 | 54 | 55 | 87 |
| 4 | Ebecryl 284 | 64 | TPGDA | 32 | 3 | 0,3 | 64 | 69 | 73 | 99 |
| 5 | Ebecryl 605 | 79 | NVP | 17 | 3 | 0,25 | 59 | 76 | 85 | 100 |
| 6 | Ebecryl 1608 | 48 | TPGDA | 48 | 3 | 0,25 | 50 | 65 | 65 | 95 |
| 7 | Photomer 4127 | 96 | | | 3 | 0,25 | 76 | 75 | | 98 |
| 8 | Ebecryl 284 | 64 | TPGDA | 32 | 3 | 0,25 | 76 | 75 | 85 | 90 |
| 9 | no coating | (control) | | | | | 100 | | | |

I claim:

1. A coated material comprising a solid substrate comprising
   a biologically or chemically active substance, and
   a permeable network coating comprising a water insoluble acrylate or methacrylate polymer formed by polymerization of a coating material comprising at least one crosslinkable polyfunctional acrylate or methacrylate compound and consisting essentially of components that are polymerized to form the network coating, said network coating being formed on at least a part of the surface of the solid substrate in a manner which substantially avoids agglomeration of the solid substrate wherein release of the active substance through the network coating is controlled.

2. A coated material according to claim 1, wherein the polyfunctional compound has the general formula $$R-(CO-\underset{R^1}{\underset{|}{C}}=CH_2)_n$$

wherein $R^1$ is H or $CH_3$, n is 2, 3, or 4, and R is a polyalcohol or a polyamine.

3. A coated material according to claim 1, wherein the coating material is a liquid mixture comprising one or more high viscosity polymerizable compounds and one or more low viscosity polymerizable compounds.

4. A coated material according to claim 3, wherein the high viscosity polymerizable compounds are selected from the group consisting of urethane-(meth)acrylates, epoxy-(meth)acrylates, polyester-(meth)acrylates, polyether-(meth)acrylates and amine-(meth)acrylates.

5. A coated material according to claim 3, wherein the low viscosity polymerizable compounds are selected from the group consisting of triisopropyleneglycoldiacrylate, 1,6-n-hexanedioldiacrylate and trismethylolpropanetriacrylate.

6. A coated material according to claim 1 having an induction period of from 1 to 9 hours.

7. A coated material according to claim 1, wherein the coating material further comprises one or more monofunctional polymerizable monomers as modifiers.

8. A coated material according to claim 7, wherein the monofunctional polymerizable monomer is N-vinyl pyrollidone.

9. A method for preparing coated materials having controlled release properties comprising
   (a) applying a coating material comprising at least one polymerizable, crosslinkable, polyfunctional acrylate or methacrylate compound to at least a part of the surface of a solid substrate in a manner which substantially avoids agglomeration of the solid substrate, said substrate comprising a biologically or chemically active substance; and
   (b) polymerizing the coating material to form a permeable network coating, wherein the coating material consists essentially of components that are polymerized to form the network coating.

10. A method according to claim 9, wherein the polyfunctional compound has the general formula

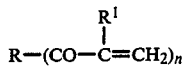

wherein $R^1$ is H or $CH_3$, n is 2, 3, or 4, and R is a polyalcohol or a polyamine.

11. A method according to claim 9, wherein the coating material comprises one or more compounds selected from the group consisting of urethane-(meth)acrylates, epoxy-(meth)acrylates, polyester-(meth)acrylates, polyether-(meth)acrylates, and amine-(meth)acrylates.

12. A method according to claim 11, wherein the coating material further comprises one or more monofunctional polymerizable monomers as modifiers.

13. A method according to claim 12, wherein the monofunctional polymerizable monomer is N-vinylpyrrollidone.

14. A method according to claim 9, wherein the coating material is formed by mixing one or more high viscosity polymerizable compounds with one or more low viscosity polymerizable compounds.

15. A method according to claim 9, wherein radiation is used to polymerize the coating material.

16. A method according to claim 15, wherein the radiation is an electron beam, gamma radiation, or ultraviolet light.

17. A method according to claim 9, wherein the substrate is a particulate solid.

18. A method according to claim 17, wherein the coating material is applied to the particulate substrate while said substrate is in a fluidized state.

19. A method according to claim 9, wherein the active substance is selected from the group consisting of drugs, flavorants, fragrances, agrochemicals, fertilizers, catalysts, enzymes and microorganisms.

20. A coated material according to claim 1, wherein the substrate is a particulate solid.

21. A coated material according to claim 20, wherein the coating material is applied to the particulate substrate while said substrate is in a fluidized state.

22. A coated material according to claim 1, wherein the active substance is selected from the group consisting of drugs, flavorants, fragrances, agrochemicals, fertilizers, catalysts, enzymes and microorganisms.

* * * * *